United States Patent
Han et al.

(10) Patent No.: US 6,701,787 B2
(45) Date of Patent: Mar. 9, 2004

(54) ACOUSTIC SENSOR FOR PIPELINE DEPOSITION CHARACTERIZATION AND MONITORING OF PIPELINE DEPOSITS

(75) Inventors: Wei Han, Missouri City, TX (US); Vimal V. Shah, Houston, TX (US); James R. Birchak, Spring, TX (US); Bruce H. Storm, Houston, TX (US); Rajnikant M. Amin, Houston, TX (US); Bayram Kalpakci, The Woodlands, TX (US); Fouad Fleyfel, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 10/223,505

(22) Filed: Aug. 19, 2002

(65) Prior Publication Data

US 2003/0024316 A1 Feb. 6, 2003

Related U.S. Application Data

(62) Division of application No. 09/851,511, filed on May 8, 2001.

(51) Int. Cl.$^7$ ............................................. G01N 29/00
(52) U.S. Cl. ...................... 73/629; 73/53.06; 73/54.25; 73/579; 73/602
(58) Field of Search ..................... 73/629, 579, 587, 73/589, 609, 625, 643, 644; 310/324

(56) References Cited

U.S. PATENT DOCUMENTS

| | | | | |
|---|---|---|---|---|
| 3,943,753 A | * | 3/1976 | Simon | 73/54 |
| 4,004,461 A | * | 1/1977 | Lynnworth | 73/194 A |
| 4,088,915 A | * | 5/1978 | Kodama | 310/334 |
| 4,145,917 A | * | 3/1979 | Brazhnikov | 73/32 R |
| 4,170,742 A | * | 10/1979 | Itagaki et al. | 310/324 |
| 4,320,659 A | * | 3/1982 | Lynnworth et al. | 73/589 |
| 5,095,754 A | * | 3/1992 | Hsu et al. | 73/602 |
| 5,179,862 A | * | 1/1993 | Lynnworth | 73/861.28 |
| 5,433,112 A | * | 7/1995 | Piche et al. | 73/597 |
| 5,661,233 A | * | 8/1997 | Spates et al. | 73/61.45 |
| 5,710,374 A | * | 1/1998 | Ross et al. | 73/54.24 |
| 6,223,588 B1 | * | 5/2001 | Burgass et al. | 73/53.01 |
| 6,311,549 B1 | * | 11/2001 | Thundat et al. | 73/54.24 |

* cited by examiner

Primary Examiner—Hezron Williams
Assistant Examiner—Jacques Saint-Surin
(74) Attorney, Agent, or Firm—Conley Rose, P.C.

(57) ABSTRACT

A method and apparatus for analyzing a deposited layer on the inner surface of a fluid container wall having inner and outer surfaces are disclosed. One embodiment of the method comprises (a) transmitting an acoustic signal from a transmitter at a first distance from the outer surface of the wall; (b) receiving a first received signal A, comprising a reflection from the wall outer surface; (c) receiving a second received signal B, comprising a reflection from the wall inner surface; (d) receiving a third received signal C from the wall inner surface; (e) calculating a coefficient $R_{wp}$ from A, B and C, and (f) calculating a coefficient $R_{pd}$ from A, B and $R_{wp}$, and calculating the acoustic impedance of the deposited layer $Z_d$ from $R_{wp}$, $R_{pd}$, and $Z_w$, where $Z_w$ is the acoustic impedance of the material between the transmitter and the wall outer surface. A preferred embodiment of the apparatus comprises a piezoelectric or ferroelectric transducer having front and back faces; a backing member acoustically coupled to said transducer back face and impedance-matched to said transducer element, said backing member having proximal and remote faces; and a delay material disposed between said transducer front face and the wall outer surface.

9 Claims, 2 Drawing Sheets

ACOUSTIC SENSOR FOR PIPELINE DEPOSITION CHARACTERIZATION AND MONITORING OF PIPELINE DEPOSITS

CROSS-REFERENCE TO RELATED APPLICATIONS

This is a divisional application of pending U.S. patent application Ser. No.09/851,511, filed May 8, 2001.

STATEMENT REGARDING FEDERALLY SPONSORED RESEARCH OR DEVELOPMENT

Not Applicable.

BACKGROUND OF THE INVENTION

As the current trend in offshore oil and gas production advances into deeper waters, it is becoming increasingly necessary for the industry to develop cost effective solutions for developing fields in deep and/or remote waters.

A typical solution for such cases is to keep the production facilities on a "host platform" and connect the deep-water well(s) to the platform with pipelines and risers. The supporting equipment for the subsea tree control, such as hydraulic and electric power units, chemical injection pumps and tanks, and a control console, are also housed on the host platform. The subsea tree control is accomplished via long umbilical(s) consisting of electric conductors, hydraulic lines and chemical injection lines laid alongside the pipeline. In addition, two parallel pipelines are necessary to accomplish the roundtrip pigging operations. The distance between the well and the host platform is known as the tieback distance. The cost and technical challenges of this type of conventional tieback system increase as the tieback distance increases, and to a lesser extent as the water depth increases. In most cases, 20 miles represents the practical limit for the maximum tieback distance with the conventional tieback system.

One limit on the length of subsea tiebacks conveying crude petroleum arises from flow assurance problems. Solids such as asphaltene and paraffin deposit on the inner walls of the tiebacks and partially, and in some cases completely, block the flow. The longer the tieback is, the greater the length of pipe that must be inspected and kept free of deposits.

At present, non-intrusive sensors that can adequately detect and characterize such deposits are not available. The present solutions require use of very expensive alternative methods for flow assurance, including twin flowlines (for round-trip pigging), heat traced or insulated tiebacks. These alternative methods operate by attempting to prevent the deposition of solids on the flowline wall, and do not provide means for detecting the presence of solids in the event that deposits occur. The lack of continuous monitoring can result in undesirable shutdowns. For example, a flowline has been kept clear by pigging at a certain frequency, e.g. once per month, and the composition of the fluid in the flowline changes so that deposits begin to form at a greater rate, the line will become clogged and possible shut down because the previously established pigging frequency is now insufficient.

Guided acoustic waves similar those described in U.S. Pat. No. 5,892,162, have been used to detect corrosion in pipes based on reflections from corroded regions. Corrosion and scaling has also been detected in insulated pipelines on surface using guided waves and literature regarding this has been published from Imperial College, University of London.

Monitoring devices such as that described in U.S. Pat. No. 4,490,679 identify paraffin by monitoring change in the resistance of an electromagnetic coil. The monitoring device requires access to the fluid and is housed in a recess in the pipe. It is desired to provide monitoring without disrupting the flow of fluid through the line and without requiring direct contact with the fluid.

In U.S. Pat. No. 4,483,247, an optical asphaltene sensor is described. This sensor determines the content of asphaltene in heavy oils, based on the absorption spectra of asphaltene. The invention uses visible light in the region 500 nm to 1000 nm and thus requires at least optical access to the fluid. Furthermore, it does not distinguish between deposited and suspended asphaltene solids.

Similarly, ultrasonic longitudinal wave measurements have been used to characterize fluids using reflectance methods, as in U.S. Pat. No. 4,571,693. Shear reflectance has been used in prior art to monitor casting processes as in U.S. Pat. No. 5,951,163, detect viscosity as in U.S. Pat. No. 3,903,732, or density as in U.S. Pat. No. 5,886,250 and to monitor the rheology of fluids.

Hence, it is desired to provide a system that can operate over greater tieback distances without the cost and technical disadvantages that heretofore have prevented increasing the tieback distance. It is further disired to provide a method and apparatus for detecting and characterizing deposits of asphaltene, paraffin or hydrates on the inside wall of a pipeline. It is further desired to provide a system that can be installed on a conventional pipeline and does not impede the flow of fluid through the pipeline. The desired system should be able to compensate for drift in the response of its components and should be capable of operating for a period of years without service or calibration.

SUMMARY OF THE INVENTION

The present invention provides a method and apparatus that allows non-invasive monitoring of longer tieback distances without the cost and technical disadvantages associated with previous methods. The system of the present invention measures the acoustic properties of deposits on the inner surface of the pipe wall. One object of the invention is to detect, characterize and determine the extent of deposition and thus enable remedial procedures.

The present system detects deposits or deposition of asphaltene and paraffin on the inside wall of a pipeline without impeding the flow of fluid through the pipeline. Furthermore, the present system compensates for drift in the response of its components and is therefore capable of operating for period of years without service or calibration.

In particular, the present system includes an acoustic sensor that is capable of detecting and characterizing deposits of paraffin, asphaltene or hydrates on the inner walls of pipes, thus enabling timely intervention and flow assurance. In one embodiment, the sensor detects and monitors deposition in a section of the pipe. In another embodiment, multiple installations of the system allow the location of depositions to be determined with a desired degree of precision.

The present apparatus is capable of self-calibration and is not affected by drifts in equipment response that may be caused by variations in temperature or pressure or by the passage of time. The present sensors distinguish between types of deposition material based on the frequency and phase response.

In one embodiment, the present system is used to monitor and characterize the deposition and build-up of materials such as paraffin, asphaltene and hydrates in subsea tiebacks. Alternatively, the present system can be permanently installed in a borehole to monitor deposition therein. The present sensor can also be used on surface pipelines to monitor deposition of solids in cases where solids deposition may occur, such as multiphase flow.

In a preferred embodiment, the sensor distinguishes the type of deposition material based on the compression and shear impedance as well as signal arrival times.

BRIEF DESCRIPTION OF THE DRAWINGS

For a more detailed understanding of the invention, reference will be made to the accompanying Figures, wherein.

DETAILED DESCRIPTION OF THE PREFERRED EMBODIMENTS

Two methods of measuring acoustic impedance of deposits based on acoustic reflectance (longitudinal or shear) are disclosed here. In the first method, deposition impedance is computed from the amplitude of reflected acoustic signal arriving from the delay wedge/pipe wall interface and the wall-deposition interface. The other method additionally measures acoustic reflection from the remote end of the transducer backing and uses the reflected amplitude as a reference.

Transmitter-Receiver Arrangement

Figure 1:
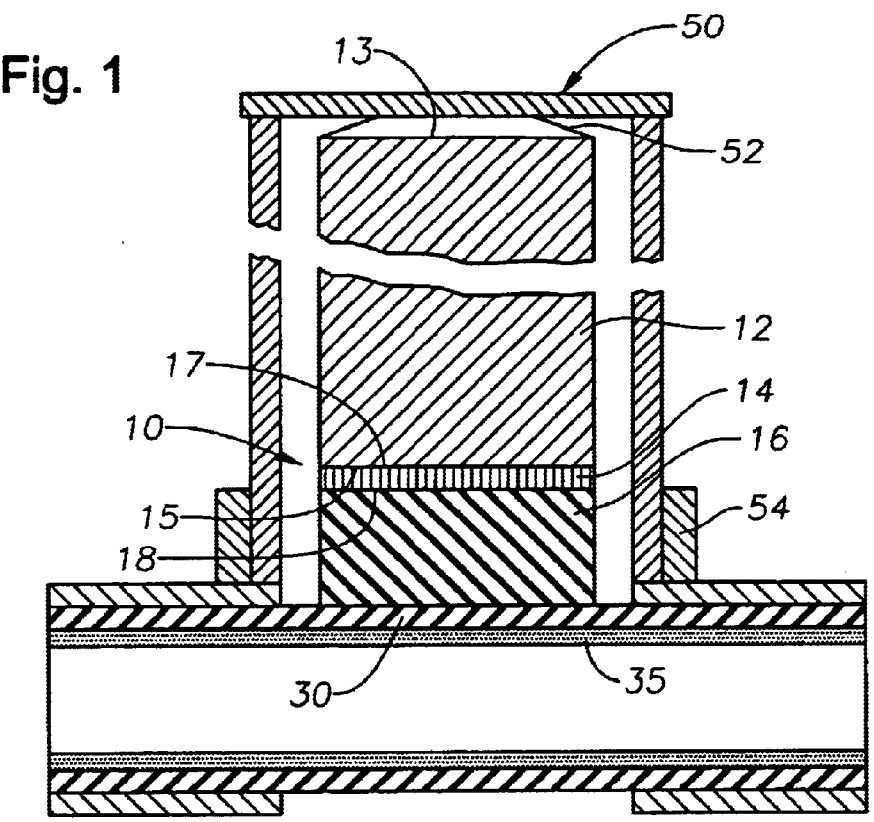
FIG. 1 is a cross-sectional view of an apparatus according to a first embodiment of the present invention mounted on a pipe.

Referring initially to FIG. 1, a preferred embodiment of the present transducer system includes a piezoelectric or ferroelectric transducer block 10, the wall of the pipe 30, and a layer of deposited solid or semi-solid material 35, as shown in FIG. 1. Transducer block 10 preferably comprises an impedance matched backing solid 12, piezoelectric or ferroelectric element (PZT) 14, and a delay wedge 16, which is preferably impedance matched with PZT 14. The outer end 13 of backing 12 is exposed to a fluid medium (such as air or water), while the inner end 15 is fixed to the outer face 17 of PZT 14. In one preferred embodiment, backing solid 12 is designed so that the distance between ends 13, 15 is great enough to ensure that reflections from outer end 13 will not overlap with the reflected signals from other interfaces, including the wedge 16/pipe wall 30 interface, and the pipe wall 30/deposit 35 interface. The inner end 18 of PZT 14 is acoustically coupled to delay wedge 16, which preferably has an acoustic impedance close to the acoustic impedance of PZT 14. The function of wedge 16 is to produce a reflection at the wedge-pipe wall interface, which helps in characterizing the pipe wall, as discussed below. The delay wedge 16 preferably comprises of titanium or alloys of titanium with acoustic impedance close to the acoustic impedance of PZT 14.

It is necessary to calibrate reflection coefficients in order to accurately measure the impedance of the deposit 35 (longitudinal and/or shear). In particular, temperature and material property variations that cause pipe wall impedance variations must be compensated for. An implicit compensation method is discussed in the following paragraphs.

Delay wedge 16 is preferably constructed of an elastic material. Its temperature-dependent longitudinal and shear impedance are known, e.g. from lab measurements. The deposited materials 35 are typically visco-elastic in nature.

A clamp or retaining device 50 is used to maintain good acoustic coupling between transducer block 10 and the pipe wall 30. One or more Belleville springs 52 or other biasing means may be positioned between clamp 50 and transducer block 10 to urge block 10 toward pipe 30. Clamp 50 may be held together with the pipe by a threaded sleeve 54, wherein the end of the clamp 50 mates with the rising section of sleeve 54. Sleeve 54 clamps circumferentially on the outside of the pipe. Clamp 50 could be designed to allow pressure balancing.

Figure 2:
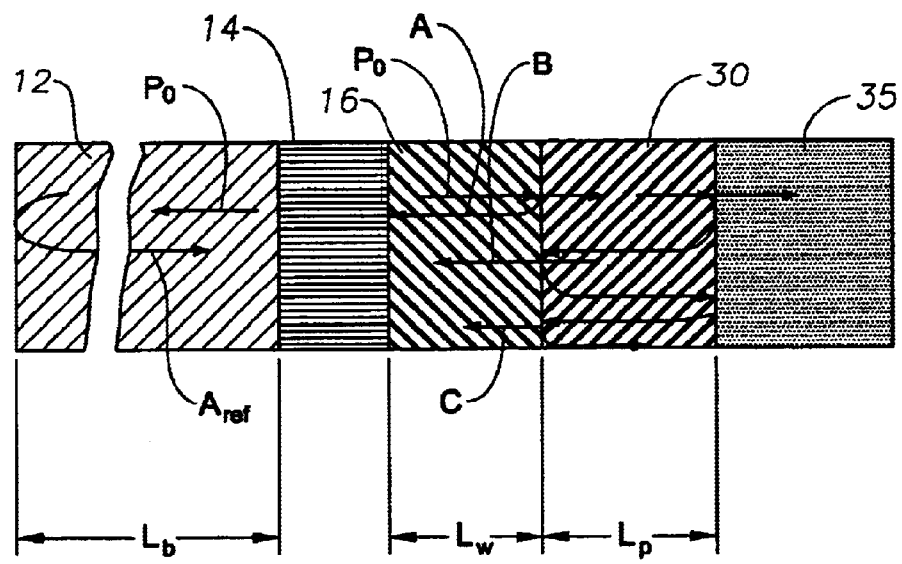
FIG. 2 is a schematic diagram showing propagation and reflection of an acoustic signal through the components of the apparatus of FIG. 1.
Figure 3:
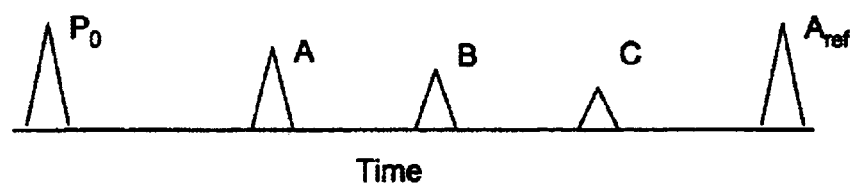
FIG. 3 is a representation of the signals received as a result of the reflections shown in FIG. 2.

Referring now to FIGS. 2 and 3, PZT 14 emits an incident acoustic signal $P_0$. A portion of the signal $P_0$ is reflected back from each of the interfaces across which it travels. Thus, PZT 14 measures several reflections from various interfaces. There signals are labeled in FIGS. 2 and 3 as A—reflection from the delay wedge 16/wall 30 interface, B—first reflection echo from the wall 30/deposit 35 interface, and C second reflection from the wall 30/deposit 35 interface. If $Z_w$ and $Z_p$ are the (either longitudinal or shear) impedances of the wedge and wall, respectively, the reflection coefficient of the wedge/wall interface $R_{wp}$ can be written as $$R_{wp} = \frac{Z_p - Z_w}{Z_p + Z_w}$$

$R_{wp}$ can also be written in terms of the three reflected signals A, B and C, as $$R_{wp} = \sqrt{\frac{A \cdot C}{A \cdot C - B^2}}$$

The impedance $Z_w$ of delay wedge 16 is known and depends on the selection of the wedge material. Hence, the coefficient $R_{wp}$ can be determined from A, B and C are used to compute $Z_p$.

The reflection coefficient of the wall 30/deposit 35 interface $R_{pd}$, can be given by $$R_{pd} = \frac{B}{A} \frac{R_{wp}}{(1 - R_{wp}^2)} e^{2L_p \alpha_p}$$

where, $L_p$ and $\alpha_p$ are the thickness and attenuation of the pipe wall, respectively. Once $R_{wp}$ and $R_{pd}$ are determined, the acoustic impedance of the deposited layer 35, $Z_d$ is preferably determined by $$Z_d = Z_w \frac{1 + R_{wp}}{1 - R_{wp}} \cdot \frac{1 + R_{pd}}{1 - R_{pd}}$$

where, $Z_w$ is the impedance (longitudinal or shear) of delay wedge 16.

In this manner, the longitudinal and/or shear impedance of the deposited material (e.g. wax) can be determined from the measurable amplitude of the reflected delay wedge 16/wall 30 echo A and the amplitudes of the first and second reflected echoes B and C.

One advantage provided by the present invention is that, in determining the acoustic impedance of deposition, it avoids the need to use reference signals that may be generated by acoustic delay lines with notches, slots and holes as reflectors such as are commonly used in the prior art, such as U.S. Pat. No. 4,571,693. Notches and slots introduce undesirable non-uniform scattering of the acoustic waves. In addition, the notched or slotted delay lines used in the art require careful handling during construction because of their reduced strength.

In an alternative approach, reflected acoustic waves from the outer end 13 of backing 12 are used as a reference signal $A_{ref}$ (FIG. 2). This method is useful in the circumstances where the second wall/deposit reverberation signals are either weak or overlap with the first wall/deposit echo. In this approach, backing solid 12 is preferably relatively long. For instance, the length of backing solid 12, $L_b$, preferably equals at least six times the total length of delay wedge 16 $L_w$ plus the wall thickness $L_p$, i.e. $L_b \geq 6(L_w + L_p)$. This enables the reference signal to arrive later compared to reflections from other interfaces. The far side of the backing may be exposed to an unchanging media, preferably air, in order to maintain a constant reflection coefficient. The pipe wall impedance $Z_p$ is given as $$Z_p = \frac{1 - |A/A_{ref}|}{1 + |A/A_{ref}|} Z_w$$

where A is the reflection from the delay wedge/wall interface, and $A_{ref}$ is the reference signal from the outer face of the backing solid. Then, deposition impedance can be calculated from the absolute values of B and $A_{ref}$, for small attenuation of pipe wall material, as $$Z_d = \frac{1 - \frac{(Z_w + Z_p)^2}{4Z_w Z_p}|B/A_{ref}|}{1 + \frac{(Z_w + Z_p)^2}{4Z_w Z_p}|B/A_{ref}|} Z_p$$

where B is the first reflection echo from the wall 30/deposit 35 interface.

Therefore, from the above two approaches, when a longitudinal-wave or a shear-wave transducer is used, longitudinal or shear impedance of the deposition, i.e., density× longitudinal (or shear) speed of sound, can be measured. Deposition material (as paraffin, asphaltene, hydrates) are usually regarded as visco-elastic material with both bulk module and shear module. The shear impedance consists of a real part and an imaginary part. The real part (density× shear speed of sound) can be determined from the above approaches. The imaginary part of the shear impedance, which is a product of the viscosity and density of the deposited material and the wave frequency, can be determined separately from measurement of the phase shift of the reflection coefficient due $$R \cdot e^{i\phi} = \frac{Z_{ps} - \sqrt{i\omega\rho\eta}}{Z_{ps} + \sqrt{i\omega\rho\eta}}$$

where,
to the deposit as follows;
ϕ is the phase difference between the the incident and reflected signals,
R is the absolute reflection coefficient,
$Z_{ps}$ is the shear impedance of the pipe wall These measurements provide the acoustic longitudinal and shear impedance, and phase shift of the acoustic waves due to visco-elasticity of the deposition. This information is combined to characterize the type of deposit based on the measured longitudinal (and shear) impedance of the deposit.

The present invention provides several advantages over prior art systems. These include but are not limited to:
non-invasive and non-intrusive detection, identification, characterization and monitoring of deposits in real-time.
low assurance monitoring and assessment of intervention based on deposit characteristics.
quantitative monitoring of deposits in critical areas.
compensation for variation in signal amplitude over a prolonged period of time (signal drift).
potential for use with existing tubing (retrofitting).

In a preferred embodiment, a primary application of the present system is to monitor and characterize deposition and build-up of materials such as paraffin, asphaltene, hydrates and infiltrated sand in subsea tiebacks. The present system can also be used to advantage in smart wells, where it is permanently installed in a borehole and interfaced with a microprocessor to monitor deposition. This sensor can also be used on surface pipelines to monitor deposition of solids in multiphase flow.

Compression acoustic impedance is a function of the layer density and speed of sound. Shear acoustic impedance is a function layer density and viscosity. The phase of the acoustic reflections depends on the damping properties (viscosity in oil and visco-elasticity in asphaltene, paraffin, etc.) of the deposit. Thus, based on the effect of the deposition layer on the compression and shear wave reflectance, an inverse solution calculates the deposition layer properties and indentifies composition.

Figure 4:
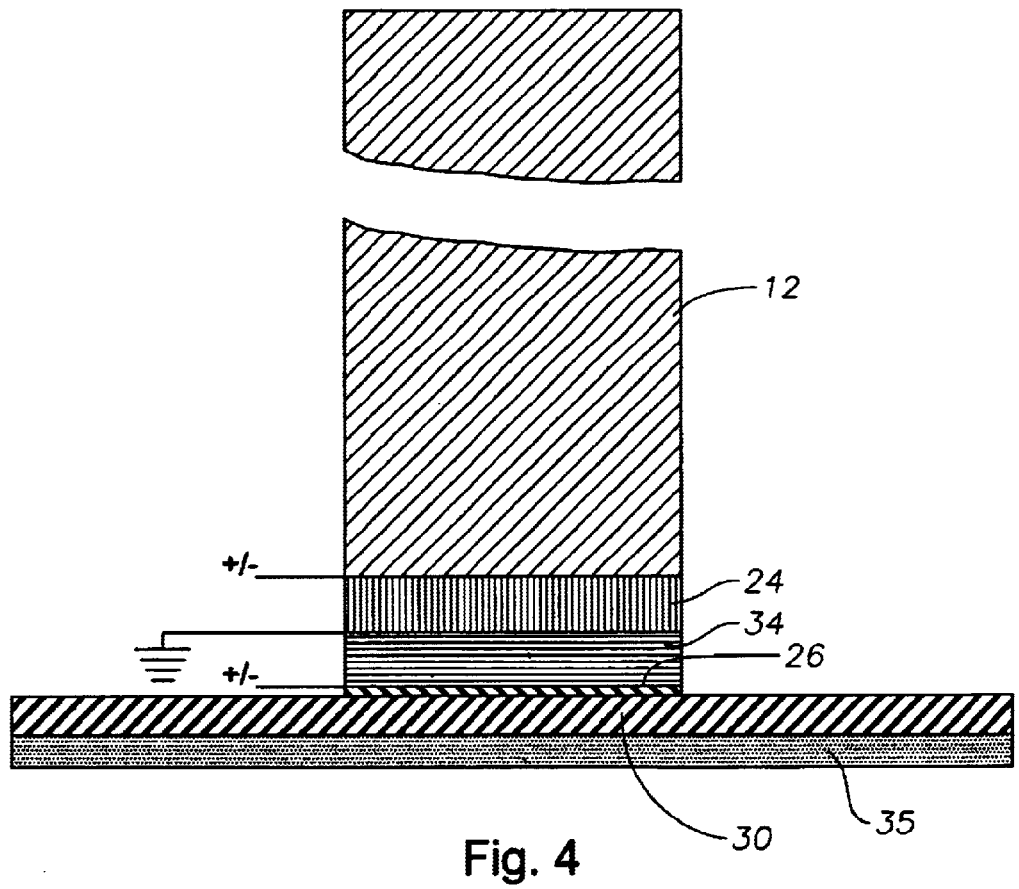
FIG. 4 is a cross-sectional view of an apparatus according to an alternative embodiment of the present invention.

In an alternative embodiment shown in FIG. 4, the acoustic sensor comprises both a compression-piezoelectric element 24 and a shear-piezoelectric element 34. A pressure clamp like clamp 50 of FIG. 1 is preferably used, but is not shown in FIG. 4. Piezoelectric elements 24, 34 are preferably bonded together and have a common-ground electrode. The relative positions of the shear and compression elements can be reversed from those shown in the Figure. The back of the upper element is preferably coupled to impedance-matched backing 12. An elastomer 26 preferably acoustically couples the element to the pipe wall. This construction is advantageous because the probe interrogates the same layer of deposition with both compression and shear waves.

The following are some preferred embodiments of the invention:
an acoustic transducer that can be clamped on the exterior of existing pipe, consisting of impedance-matched backing solid, a piezoelectric or ferroelectric transducer element, and a delay wedge. The far end of the backing is exposed to a fluid medium, while the near end is fixed to the frontal face of the piezoelectric element. The transducer system is capable of compensating for the pipe wall material property variations by measuring multiple reflections from the pipe wall and far end of the backing solid.
an acoustic device capable of generating and detecting compression and/or shear acoustic waves, which reflect from several reflecting interfaces including the interface between the pipe wall and deposits on the inner walls of pipes that are transporting crude petroleum.
an active acoustic sensor capable of characterizing the type of deposition on the inner wall of pipes, based on frequency-dependent phase and amplitude information in the reflected acoustic waves.
an active acoustic sensor capable of estimating thickness of the deposition and thus monitoring the layer buildup, based on the arrival time of the reflected wave from the deposit/fluid interface.

an acoustic sensor capable of monitoring deposition layer buildup and triggering alarms for remedial action in case the deposition thickness exceeds a pre-determined thickness.

an acoustic wave sensor that is capable of compensating for variation in signals over a period of time by using reflections from the far end of the backing material as a reference.

While preferred embodiments of the present invention have been disclosed and discussed herein, it will be understood that various modifications can be made in these embodiments without departing from the scope of the invention. For example, the principles described herein can be used to determine the presence and nature of buildup or deposits on walls other than pipeline walls, including but not limited to container walls. The present apparatus can be used to detect buildup or deposits on inner or outer walls, depending on how the apparatus is used. The dimensions and/or relative proportions of the components of the apparatus can be modified, as can the number and frequency of signals that are emitted, detected and/or analyzed by the apparatus. In the claims that follow, any recitation of steps is not intended as a requirement that the steps be performed sequentially, or that one step be completed before another step is begun, unless explicitly so stated.

What is claimed is:

1. An acoustic device for measuring buildup on a container wall having inner and outer surfaces, comprising:
    a piezoelectric or ferroelectric transducer having front and back faces, wherein the front face is oriented facing the container wall;
    a backing member acoustically coupled to said transducer back face and impedance-matched to said transducer element, said backing member having proximal and remote faces; and
    a delay material disposed between said transducer front face and the wall outer surface; wherein the device characterizes the buildup based on frequency-dependent phase and amplitude information in reflected acoustic waves.

2. The device according to claim 1, wherein the distance between the proximal and remote backing faces is at least six times the distance between the transducer front face and the wall inner surface.

3. An acoustic device for measuring buildup on a container wall having inner and outer surfaces, comprising:
    a first piezoelectric or ferroelectric transducer having front and back faces; and
    a second piezoelectric or ferroelectric transducer having front and back faces; one of said first and second transducers being capable of generating shear waves in the container wall and the other of said first and second transducers being capable of generating compression waves in the container wall; wherein the device characterizes the buildup based on frequency-dependent phase and amplitude information in the reflected acoustic waves.

4. The device according to claim 3; further including a backing member acoustically coupled to the back face of one of said transducers and impedance-matched to said transducer.

5. The device of claim 3, further including a delay material disposed between the front face of one of said transducers and the wall outer surface.

6. The device according to claim 3; wherein said first transducer is disposed between said second transducer and said container wall.

7. The device according to claim 6, further including a backing member acoustically coupled to the back face of said second transducer and impedance-matched to said second transducer.

8. The device according to claim 6, further including a delay material disposed between the front face of said first transducer and the container wall.

9. The device according to claim 6, further including an elastomeric material disposed between the front face of said first transducer and the container wall.

* * * * *